（12）United States Patent
Callahan (10) Patent No.: US 10,702,618 B2
(45) Date of Patent: Jul. 7, 2020

(54) DISINFECTION SYSTEMS AND METHODS FOR OPERATING A LIGHT SYSTEM

(71) Applicant: The Boeing Company, Chicago, IL (US)

(72) Inventor: Kevin S. Callahan, Everett, WA (US)

(73) Assignee: The Boeing Company, Chicago, IL (US)

( * ) Notice: Subject to any disclaimer, the term of this patent is extended or adjusted under 35 U.S.C. 154(b) by 153 days.

(21) Appl. No.: 15/633,121

(22) Filed: Jun. 26, 2017

(65) Prior Publication Data
US 2018/0369434 A1 Dec. 27, 2018

(51) Int. Cl.
*A61L 2/10* (2006.01)
*A61L 2/24* (2006.01)
*A61L 2/26* (2006.01)

(52) U.S. Cl.
CPC .......... *A61L 2/10* (2013.01); *A61L 2/24* (2013.01); *A61L 2/26* (2013.01); *A61L 2202/11* (2013.01); *A61L 2202/14* (2013.01); *A61L 2202/25* (2013.01); *A61L 2209/12* (2013.01)

(58) Field of Classification Search
CPC ................. A61L 2/10; A61L 2/26; A61L 2/24
See application file for complete search history.

(56) References Cited

U.S. PATENT DOCUMENTS

| | | | |
|---|---|---|---|
| 5,483,127 A | 1/1996 | Widmayer | |
| 6,877,248 B1 * | 4/2005 | Cross | D06F 58/203 34/275 |
| 8,138,690 B2 * | 3/2012 | Chemel | F21V 17/02 315/318 |
| 8,339,069 B2 * | 12/2012 | Chemel | H05B 37/029 315/294 |
| 8,368,321 B2 * | 2/2013 | Chemel | H05B 37/029 315/294 |
| 8,543,249 B2 * | 9/2013 | Chemel | H05B 37/0272 351/51 |
| 8,552,664 B2 * | 10/2013 | Chemel | H05B 37/0245 315/291 |

(Continued)

OTHER PUBLICATIONS

Co-pending U.S. Appl. No. 15/237,710, filed Aug. 16, 2016.
(Continued)

*Primary Examiner* — Regina M Yoo
(74) *Attorney, Agent, or Firm* — McDonnell Boehnen Hulbert & Berghoff LLP (57) ABSTRACT

In an example, a method of operating a UV light source for a vehicle includes measuring an amount of power on a commodity power feeder, determining when the measured amount of power is greater than a threshold amount of power and, responsively, actuating a switch to a first state in which the switch decouples the UV light source from the power on the commodity power feeder. The method also includes determining when the measured amount of power is less than the threshold amount of power and responsively actuating the switch to a second state in which the switch couples the UV light source to the power on the commodity power feeder. The method also includes, while the switch is in the second state, activating the UV light source, using the power from the commodity power feeder, to emit UV light in the vehicle.

20 Claims, 8 Drawing Sheets

(56) References Cited

U.S. PATENT DOCUMENTS

| | | | |
|---|---|---|---|
| 8,593,135 B2* | 11/2013 | Chemel | H05B 37/029 324/105 |
| 8,805,550 B2* | 8/2014 | Chemel | H05B 37/029 315/51 |
| 8,954,170 B2* | 2/2015 | Chemel | H05B 37/029 315/297 |
| 9,623,133 B2 | 4/2017 | Childress et al. | |
| 9,700,072 B2 | 7/2017 | Dobrinsky et al. | |
| 9,783,974 B1 | 10/2017 | Tillotson | |
| 10,145,055 B1* | 12/2018 | Harlan | D06F 58/203 |
| 2006/0163135 A1* | 7/2006 | Ellis | D06F 35/001 210/251 |
| 2010/0193629 A1 | 8/2010 | Breit et al. | |
| 2011/0057123 A1* | 3/2011 | Ho | H02J 7/025 250/492.1 |
| 2013/0330235 A1 | 12/2013 | Stibich et al. | |
| 2014/0266695 A1* | 9/2014 | Addison | A61B 5/7405 340/539.12 |
| 2016/0195427 A1 | 7/2016 | Vance et al. | |
| 2016/0220716 A1 | 8/2016 | Childress et al. | |
| 2016/0250362 A1 | 9/2016 | Mackin | |
| 2017/0107659 A1 | 4/2017 | Hills | |
| 2017/0283062 A1 | 10/2017 | Childress | |
| 2017/0283092 A1 | 10/2017 | Brown et al. | |
| 2017/0284076 A1 | 10/2017 | Jensen | |

OTHER PUBLICATIONS

Co-pending U.S. Appl. No. 15/241,438, filed Aug. 19, 2016.
Co-pending U.S. Appl. No. 15/245,251, filed Aug. 24, 2016.
Co-pending U.S. Appl. No. 15/259,685, filed Sep. 8, 2016.
Co-pending U.S. Appl. No. 15/271,349, filed Sep. 21, 2016.
Co-pending U.S. Appl. No. 15/273,814, filed Sep. 23, 2016.
Co-pending U.S. Appl. No. 15/632,968, filed Jun. 26, 2017.
Co-pending U.S. Appl. No. 15/633,028, filed Jun. 26, 2017.
Co-pending U.S. Appl. No. 15/633,085, filed Jun. 26, 2017.
Co-pending U.S. Appl. No. 15/633,142, filed Jun. 26, 2017.

* cited by examiner

DISINFECTION SYSTEMS AND METHODS FOR OPERATING A LIGHT SYSTEM

FIELD

The present disclosure generally relates to systems and methods for light systems, and more particularly to systems and methods for operating an ultraviolet (UV) light source to disinfect an environment.

BACKGROUND

Pathogens may be spread between humans, between animals, or between humans and animals in many different ways. Consequently, there is an increasing need for the disinfection of public environments. One approach for disinfecting an environment involves irradiating the environment with ultraviolet (UV) light using a UV light source.

SUMMARY

In an example, a disinfection system for a vehicle is described. The disinfection system includes a UV light source configured to emit UV light in the vehicle, and a switch configured to selectively couple the UV light source to a commodity power feeder. The commodity power feeder provides power from a power source of the vehicle to a commodity system of the vehicle. The switch is actuatable between a first state in which the switch decouples the UV light source from the power on the commodity power feeder, and a second state in which the switch couples the UV light source to the power on the commodity power feeder. The disinfection system also includes a power sensor configured to measure an amount of power on the commodity power feeder, and a control device in communication with the power sensor and the switch.

The control device is configured to: (i) determine when the measured amount of power is greater than a threshold amount of power, (ii) responsive to a determination that the measured amount of power is greater than the threshold amount of power, actuate the switch to the first state, (iii) determine when the measured amount of power is less than the threshold amount of power, and (iv) responsive to a determination that the measured amount of power is less than the threshold amount of power, actuate the switch to the second state.

In another example, a method of operating a UV light source for a vehicle is described. The method includes measuring an amount of power on a commodity power feeder, which provides the power from a power source of the vehicle to a commodity system of the vehicle. The method also includes determining when the measured amount of power is greater than a threshold amount of power. The method further includes responsive to determining that the measured amount of power is greater than the threshold amount of power, actuating a switch to a first state in which the switch decouples the UV light source from the power on the commodity power feeder. Additionally, the method includes determining when the measured amount of power is less than the threshold amount of power and, responsive to determining that the measured amount of power is less than the threshold amount of power, actuating the switch to a second state in which the switch couples the UV light source to the power on the commodity power feeder. The method also includes, while the switch is in the second state, activating the UV light source, using the power from the commodity power feeder, to emit UV light in the vehicle.

In another example, a method of operating a UV light source is described. The method includes providing, on a commodity power feeder, power from a power source of a vehicle to a galley system of the vehicle, measuring an amount of power on the commodity power feeder, and determining that the measured amount of power is less than a threshold amount of power. The method also includes, responsive to determining that the measured amount of power is less than the threshold amount of power, coupling the UV light source to the power on the commodity power feeder. The method further includes while coupling the UV light source to the power on the commodity power feeder, using the power on the commodity power feeder to simultaneously (i) activate the UV light source to emit UV light in a lavatory of the vehicle and (ii) operate an electrical device in the galley system. Additionally, the method includes while activating the UV light source and operating the electrical device, determining that the measured amount of power is greater than the threshold amount of power. The method also includes, responsive to determining that the measured amount of power is greater than the threshold amount of power, decoupling the UV light source from the power on the commodity power feeder to deactivate the UV light source while continuing to operate the electrical device in the galley system.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

The systems and methods of the present disclosure provide disinfection systems for a vehicle and methods for operating a UV light source for a vehicle. When activated, the UV light source emits UV light, which can kill and/or disable microorganisms such as bacteria, viruses, molds, and/or other pathogens. For example, when microorganisms are exposed to a sufficiently high dose of UV light, the UV light can damage nucleic acids and/or disrupt the deoxyribonucleic acid (DNA) of the microorganisms, rendering the microorganisms unable to carry out cellular functions and infect people.

In general, the UV light source receives power from a power source of the vehicle and converts the power into the UV light. The power source may also provide power to other commodity systems of the vehicle. For example, an aircraft can have a power source that also provides power to, among other commodity systems, one or more motor flight control systems, electronic engine control systems, communication systems, navigation systems, cabin lighting systems, closet lighting systems, passenger service unit systems, audio visual systems, lavatory systems, and/or galley systems. More generally, a commodity system is an electrical device and/or system of the vehicle that is powered by a power source of the vehicle. To meet the power requirements of the various commodity systems, the vehicle can include an electrical distribution system that provides specific portions of the power supplied by the power source to the commodity systems in accordance with a power budget.

A challenge is presented when a vehicle is to be retrofitted with the UV light source as the power requirements of the UV light source may not have been taken into consideration when the power budget and electrical distribution system were designed. As one example, it may desirable to retrofit a vehicle with a UV light source in a lavatory of the vehicle. In this example, however, the power requirements of the UV light source may exceed the power that is provided by the electrical distribution system to the lavatory.

One approach to providing the UV light source with sufficient power is to run an additional power feeder (e.g., a conductor) from the power source to the UV light source. However, in some vehicles, the distance between the power source and the UV light source can be relatively long, and thus it may be costly and/or difficult to install the additional power feeder. For instance, on an aircraft, the additional power feeder may need to be run from an electrical equipment bay at a fore position of the aircraft (e.g., below the flight deck of the aircraft) to a lavatory at an aft position of the aircraft (e.g., at the aft-most portion of a passenger cabin). In such a scenario, the additional power feeder may have a length that is equal to or greater than approximately 100 feet (ft).

Similar challenges may also be encountered during an initial buildout of a new vehicle. For instance, providing an additional power feeder dedicated to the UV light source may be costly given that the UV light source may be operated relatively infrequently. Additionally, for instance, if the UV light source is specifically accounted for in the power budget as a separate system, the vehicle may require a power source with greater energy supply capabilities. This can lead to an increased size and/or weight of the power source, which may be undesirable in some implementations.

The disinfection systems and methods described herein can beneficially overcome challenges to operating the UV light source for a vehicle. Within examples, the disinfection systems and methods of the present disclosure include a UV light source, a switch, a power sensor, and a control device. The power sensor can measure an amount of power on a commodity power feeder, which provides power from a power source of the vehicle to a commodity system of the vehicle (e.g., a galley). The control device can compare the measured amount of power to a threshold amount of power and, based on the comparison, control a state of the switch between a first state and a second state. In the first state, the switch decouples the UV light source from the power on the commodity power feeder. Whereas, in the second state, the switch couples the UV light source from the power on the commodity power feeder.

Within examples, the threshold amount of power can be related to an excess power capacity of the commodity power feeder at the time of the measurement. For instance, the threshold amount of power can be a value that is less than a peak amount of power that the commodity power feeder is configured to conduct when the commodity system is at a peak loading. In this example, the control device can actuate the switch to the first state when the measured amount of power is greater than the threshold amount of power, and the control device can actuate the switch to the second state when the measured amount of power is less than the threshold amount of power. The disinfection system described herein can thus selectively couple the UV light source to the commodity power feeder so that the UV light source can take advantage of unutilized power capacity of the commodity power feeder to disinfect an environment of the vehicle without interrupting operation of the commodity system.

Figure 1:
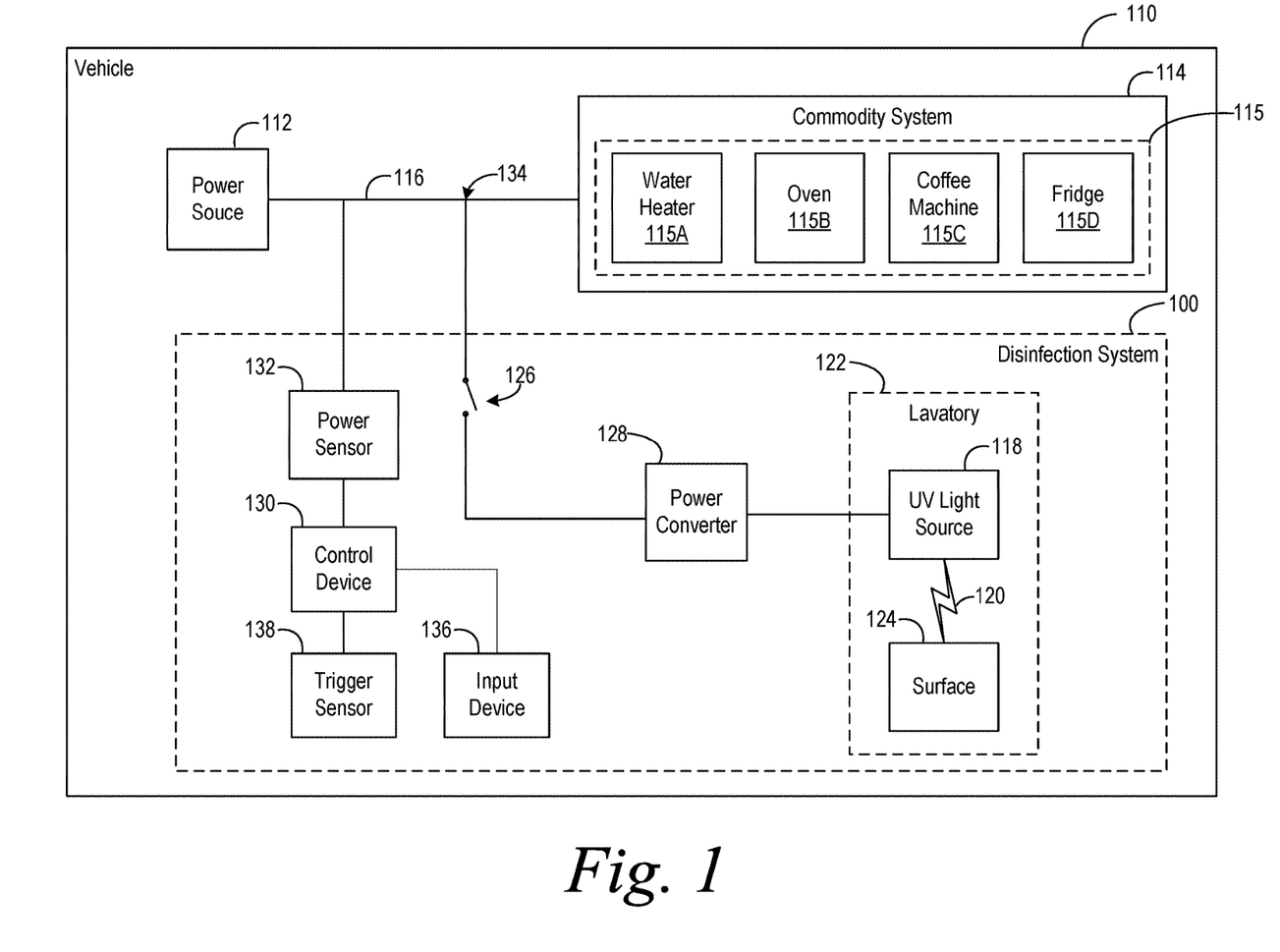
FIG. 1 illustrates a simplified block diagram of a light control system according to an example embodiment.

Referring now to FIG. 1, a disinfection system 100 for a vehicle 110 is depicted according to an example embodiment. The vehicle 110 can be an aircraft, an automobile (e.g., a car, a truck, a bus, and/or a van), a railed vehicle (e.g., a train and/or a tram), a watercraft (e.g., a ship and/or a boat), and/or a spacecraft. As shown in FIG. 1, the vehicle 110 includes a power source 112 that provides power to various commodity systems of the vehicle 110. For instance, the power source 112 can include an engine turbine that generates electrical energy during operation of the vehicle 110.

The power source 112 is coupled to a commodity system 114 of the vehicle 110 by a commodity power feeder 116. In FIG. 1, for example, the commodity system 114 is a galley including one or more electrical devices 115, which use the power provided by the commodity power feeder 116 to store, prepare, and/or cook food and/or beverages. For instance, in FIG. 1, the commodity system 114 includes a water heater 115A, an oven 115B, a coffee machine 115C, and/or a refrigerator 115D. Although, the example commodity system 114 is a galley in FIG. 1, the commodity system 114 can additionally or alternatively include cabin lighting systems, closet lighting systems, passenger service unit systems, and/or audio visual systems in additional or alternative examples.

In an example, the commodity power feeder 116 can include a conductor (e.g., a wire) that can conduct the power from the power source 112 to the commodity system 114. For example, the conductor of the commodity power feeder 116 can have a size that can provide a peak amount of power to the commodity system 114, which is related to a predetermined peak loading of the commodity 114. In one implementation, based on an example power budget, the commodity power feeder 116 can be configured to provide between approximately 10 kW to approximately 90 kW of power to the galley depending on the operation of devices in the galley at any given time. In this implementation, the peak amount of power is approximately 90 kW and the commodity power feeder 116 provides this peak amount of power when the water heater 115A, the oven 115B, the coffee machine 115C, and/or the refrigerator 115D are operating at the peak loading condition.

Also, as shown in FIG. 1, the disinfection system 100 includes a UV light source 118. When activated, the UV light source 118 can emit UV light 120 to disinfect an environment in the vehicle 110. In FIG. 1, the UV light source 118 is in a lavatory 122 of the vehicle 110. As such, the environment that is disinfected by the UV light 120 can include a surface 124 in the lavatory 122 (e.g., a surface of a toilet seat, a sink, a faucet, and/or a counter in the lavatory 122). The UV light source 118 can be located in additional and/or alternative environments of the vehicle 110 in additional or alternative examples. For instance, the UV light source 118 can be in a position to irradiate a food storage area, a trash receptacle, a galley work surface, a passenger seat, a food tray, an armrest, a head rest, a coat closet, and/or a door handle of the vehicle 110.

As examples, the UV light source 118 can include one or more excimer bulbs, mercury-vapor lamps, downshifting phosphor lamps, and/or light emitting diodes (LEDs). More generally, the UV light source 118 can be a light source that emits the UV light 120 at a wavelength within the UV spectrum (i.e., between approximately 10 nanometers (nm) and approximately 400 nm). In some implementations, the UV light source 118 can be a light source that emits UV light 120 at a wavelength within the far-UV spectrum (e.g., between approximately 190 nm and approximately 240 nm). For instance, in one implementation, the UV light source 118 can be a light source that emits the UV light 120 at a wavelength of approximately 222 nm. By emitting the UV light 120 at a wavelength in the far-UV spectrum, the UV light source 118 can more rapidly disinfect the environment than by emitting the UV light 120 at other wavelengths in the UV spectrum.

Also, within examples, the UV light source 118 can emit the UV light 120 at a predetermined wavelength and intensity for a predetermined exposure time to achieve a target level of antimicrobial efficacy during an activation cycle. In one example, the UV light source 118 can emit the UV light 120 at an intensity of 1 mW/cm$^2$ for an exposure time of 10 seconds to achieve the target level of antimicrobial efficacy for the activation cycle.

In one example, the target level of antimicrobial efficacy is a UV dose of approximately 10 mWs/cm$^2$. In additional or alternative examples, the target level of antimicrobial efficacy can be a UV dose between approximately 2 mWs/cm$^2$ and approximately 500 mWs/cm$^2$. Different microorganisms may have different abilities to withstand exposure to the UV light 120. In some implementations, the target level of antimicrobial efficacy can be based on a target microorganism-kill rate for one or more types of microorganisms that are targeted for disinfection by the light control system. As an example, the targeted microorganism kill rate can be approximately 80% to approximately 99.99%. For instance, the targeted microorganism-kill rate can be approximately 80%, approximately 90%, approximately 95%, approximately 99%, approximately 99.9%, and/or approximately 99.99% of the one or more target microorganisms irradiated by the UV dose.

As shown in FIG. 1, the disinfection system 100 also includes a switch 126. The switch 126 can selectively couple the UV light source 118 to the commodity power feeder 116. For example, the switch 126 can be actuatable between (i) a first state in which the switch 126 decouples the UV light source 118 from the power on the commodity power feeder 116, and (ii) a second state in which the switch 126 couples the UV light source 118 to the power on the commodity power feeder 116. For instance, the switch 126 can be closed in the first state and opened in the second state. As examples, the switch 126 can include one or more single pole single throw switches, a single pole double throw switches, a transistors, and/or diodes.

In this arrangement, when the switch 126 is in the first state, the commodity power feeder 116 conducts the power from the power source 112 to the commodity system 114. Whereas, when the switch 126 is in the second state, the commodity power feeder 116 can conduct a first portion of the power on the commodity power feeder 116 to the commodity system 114 and a second portion of the power on the commodity power feeder 116 to the UV light source 118. Accordingly, the commodity power feeder 116 can provide the power from the power source 112 to the commodity system 114 when the switch 126 is in the first state and when the switch 126 is in the second state. As such, operation of the commodity system 114 can be unaffected by operation of the disinfection system 100.

In some examples, the disinfection system 100 can further include a power converter 128 to condition the power on the commodity power feeder 116 for use by the UV light source 118. For instance, when the switch 126 is in the second state, the power converter 128 receives the power on the commodity power feeder 116 as an input power. The power converter 128 converts the input power to a supply power and outputs the supply power to the UV light source 118. In an example, the supply power can have a different alternating current (AC) waveform than the input power. For instance, the power converter 128 can modify one or more of a frequency, a voltage, a current, and/or a wattage of the AC waveform of the input power to form the supply power. In this way, the power converter 128 can adapt the power received from the commodity power feeder 116 to efficiently operate the UV light source 118, for example, at a target level of antimicrobial efficacy (e.g., at an intensity and/or for an exposure time corresponding to the target level of antimicrobial efficacy).

As also shown in FIG. 1, the disinfection system 100 can further include a control device 130 communicatively coupled to the switch 126 and a power sensor 132. The power sensor 132 can measure an amount of power on the commodity power feeder 116 and provide a sensor signal to the control device 130 indicating the amount of power measured by the power sensor 132. A one example, the power sensor 132 can include a current sensor that can measure the current draw on the commodity power feeder 116 and determine the amount of power based on the measured current and a known voltage on the commodity power feeder 116. As another example, the power sensor 132 can include a current sensor and a voltage sensor, and the power sensor 132 can determine the amount of power from the measured current and the measured voltage. As further examples, the power sensor 132 can include one or more analog wattmeters and/or digital wattmeters.

The power sensor 132 can be positioned along the commodity power feeder 116 between the power source 112 and a point 134 at which the switch 126 couples to the commodity power feeder 116. In this way, the power sensor 132 can measure the power on the commodity power feeder 116, which is drawn by both the commodity system 114 and the UV light source 118 when the switch 126 is in the second state. Also, in this position, the power sensor 132 can measure the power on the commodity power feeder 116, which is drawn by the commodity system 114 when the switch 126 is in the first state.

The control device 130 can receive the sensor signal from the power sensor 132, and compare the measured amount of power indicated by the sensor signal to a threshold amount of power. Based on the comparison, the control device 130 can provide a control signal to the switch 126 to actuate the switch 126 between the first state and the second state. For example, the control device 130 can determine when the measured amount of power is greater than a threshold amount of power and responsively actuate the switch 126 to the first state. Also, in this example, the control device 130 can determine when the measured amount of power is less than the threshold amount of power and responsively actuate the switch 126 to the second state.

The threshold amount of power can be related to an excess power capacity of the commodity power feeder 116 at the time the power sensor 132 measures the power on the commodity power feeder 116. For example, the threshold amount of power can be less than the peak amount of power, which is related to a predetermined peak loading of the commodity system 114. By actuating the switch 126 to the first state when the measured amount of power is greater than the threshold amount of power and actuating the switch 126 to the second state when the measured amount of power is less than the threshold amount of power, the UV light source 118 can use excess power capacity of the commodity power feeder 116 without sacrificing and/or interrupting operation of the commodity system 114.

In one example, the threshold amount of power can be approximately 50% to approximately 95% of the peak amount of power. For instance, the threshold amount of power can be approximately 50%, approximately 55%, approximately 60%, approximately 65%, approximately 70%, approximately 75%, approximately 80%, approximately 85%, approximately 90%, and/or approximately 95% of the peak amount of power.

Within examples, the threshold amount of power can be based on one or more factors such as, for instance, the peak amount of power relative to the power requirements of the UV light source 118 and/or an expected rate at which the commodity system 114 can increase its loading to reach the peak loading condition. For instance, in implementations in which the power requirements of the UV light source 118 are relatively small compared to the peak amount of power, the threshold amount of power can be a relatively large percentage of the peak amount of power. Whereas, in implementations in which the power requirements of the UV light source 118 are relatively large compared to the peak amount of power, the threshold amount of power can be a relatively small percentage of the peak amount of power. In this way, the threshold amount of power can be configured to facilitate decoupling the UV light source 118 from the commodity power feeder 116 before the combined loading of the commodity system 114 and the UV light source 118 draws an amount of power that exceeds the peak amount of power, which can be conducted by the commodity power feeder 116. This can, among other things, beneficially reduce (or prevent) the risk of interrupting operation of the commodity system 114.

As one example, the peak amount of power that the commodity power feeder 116 can provide to the commodity system 114 can be 90 kW and the UV light source 118 can use 1 kW of power to emit the UV light 120 when activated. Accordingly, in this example, the power requirement of the UV light source 118 is approximately 1.1% of the peak amount of power. As such, if the threshold amount of power is approximately 90% of the peak amount of power in this example, there is a relatively low risk that the commodity system 114 will reach the peak amount of power before the control device 130 determines that the measured amount of power is greater than the threshold amount of power and responsively actuates the switch 126 to the second state to decouple the UV light source 118 from the commodity power feeder 116.

In additional or alternative examples, the threshold amount of power can be adjusted based on user input. For example, as shown in FIG. 1, the disinfection system 100 can include a user input device 136 in the vehicle 110 and in communication with the control device 130. The user input device 136 can receive a user input indicating a value of the threshold amount of power, and transmit an input signal to the control device 130 to cause the control device 130 to adjust the threshold amount of power based on the value indicated by the user input. As examples, the user input device 136 can include one or more touchscreens, buttons, keypads, keyboards, computer mice, and/or voice-controlled input devices. By adjusting the threshold amount of power based on the user input, personnel operating the aircraft can adjust operation of the disinfection system 100 based on, for example, various conditions (e.g., a stage of flight of an aircraft, whether a galley is about to be used to prepare food, and/or whether preparation of food in a galley has been completed).

In FIG. 1, the control device 130 can also control activating and deactivating the UV light source 118. For example, the control device 130 can be coupled to one or more trigger sensors 138 that can detect one or more trigger conditions and responsively generate a trigger-sensor signal indicating that the trigger condition(s) were detected. The control device 130 can (i) receive the trigger-sensor signal indicating that the trigger condition was detected, (ii) determine, based on the trigger-sensor signal, that one or more criteria are met, and (iii) responsive to the determination that the one or more criteria are met, transmit a control signal to activate the UV light source 118.

In an example, the trigger sensor(s) 138 can include a motion sensor, an occupancy sensor, a thermal sensor, an open/close sensor, an infrared sensor device, an ultrasonic sensor device, a floor pressure sensor, and/or other types of sensors. For instance, in the example in which the disinfection system 100 is located in the lavatory 122, the trigger condition(s) detected by the trigger sensor(s) 138 can include a door of the lavatory 122 being opened, the door of the lavatory 122 being closed, the lavatory 122 being occupied, and/or the lavatory 122 being unoccupied. Additionally, for example, the one or more criteria that is used by the control device 130 to determine whether to activate the UV light source 118 can include one or more criterion such as a door of the lavatory 122 being closed, the lavatory 122 being unoccupied, the lavatory 122 having been occupied a predetermined number of times since a previous activation of the UV light source 118, and/or a predetermined amount of time having passed since the previous activation of the UV light source 118.

In general, the control device 130 is a computing device that is configured to control operation of the disinfection system 100. As such, the control device 130 can be implemented using hardware, software, and/or firmware. For example, the control device 130 can include one or more processors and a non-transitory computer readable medium (e.g., volatile and/or non-volatile memory) that stores machine language instructions or other executable instructions. The instructions, when executed by the one or more processors, cause the disinfection system 100 to carry out the various operations described herein. The control device 130, thus, can receive data (including data indicated by the sensor signals and/or trigger-sensor signals) and store the data in memory as well.

In one example, the disinfection system 100 shown in FIG. 1 can include a single UV light source 118 in a single lavatory 122; however, in alternative examples, the disinfection system 100 can include a plurality of UV light sources 118 in a plurality of lavatories 122. For instance, each lavatory 122 in the disinfection system 100 can include a respective UV light source 118 that is coupled to the switch 126 (e.g., via a respective power converter 128). In such examples, the UV light sources 118 in the lavatories 122 can simultaneously emit the UV light 120 using the power received from the commodity power feeder 116 while the switch 126 is in the second state (e.g., while the control device 130 determines that the measured power is less than the threshold amount of power). In additional or alternative examples, the disinfection system 100 can include a plurality of UV light sources 118 in a single lavatory 122 that can simultaneously emit the UV light 120 using the power received from the commodity power feeder 116 while the switch 126 is in the second state.

Figure 2A:
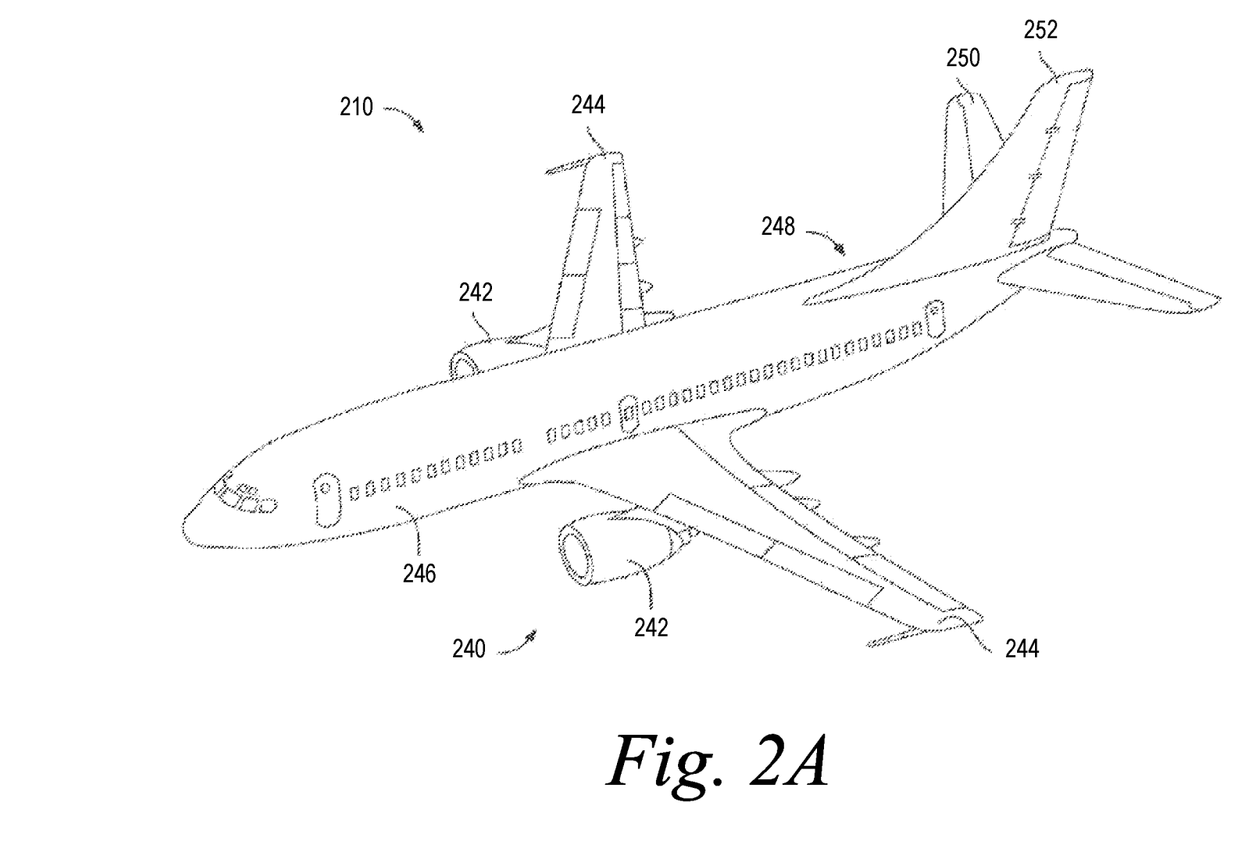
FIG. 2A illustrates a perspective view of an aircraft according to an example embodiment.
Figure 2B:
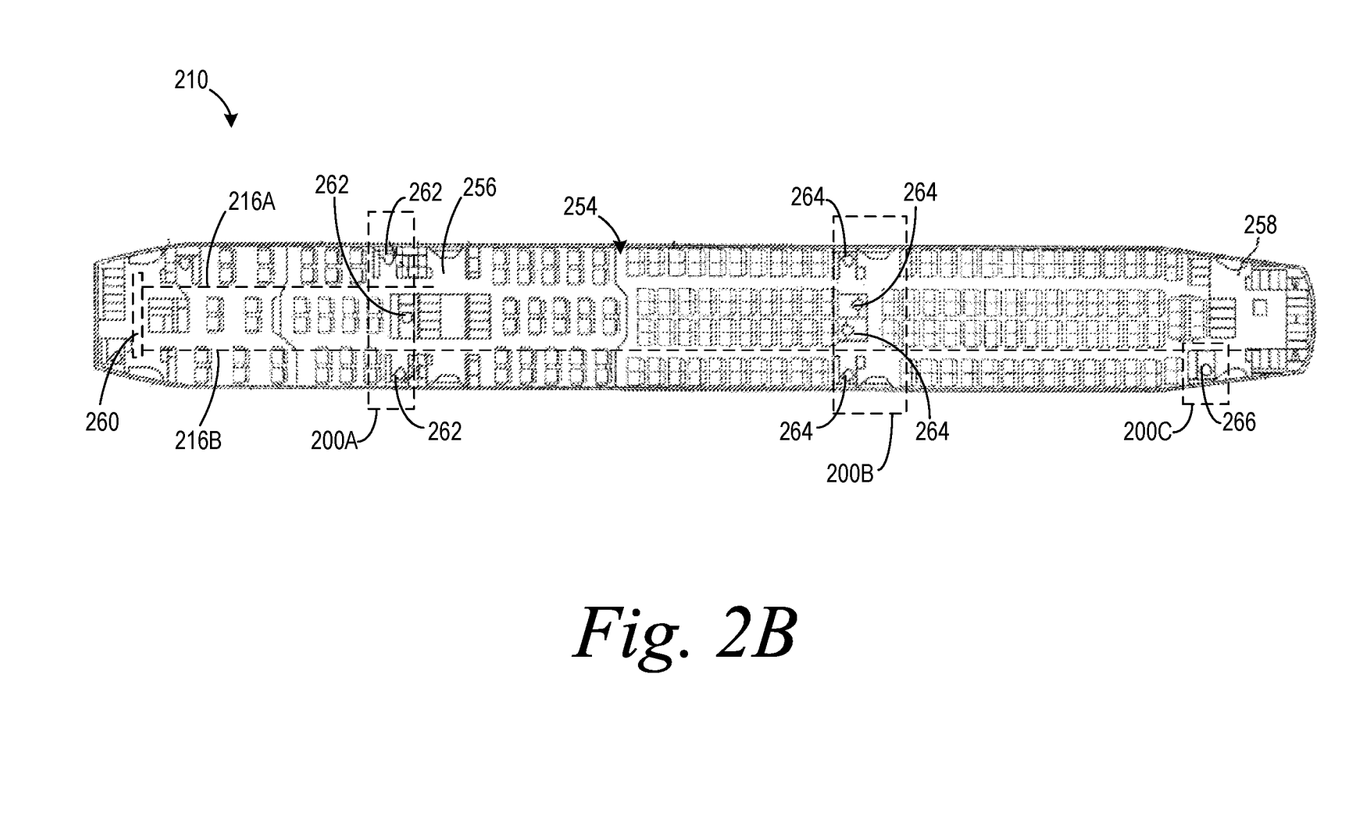
FIG. 2B illustrates a top plan view of an internal cabin of the aircraft shown in FIG. 2A.

Referring to FIGS. 2A-2B, an aircraft 210 as one example of the vehicle 110 in which the disinfection system 100 described above can be implemented and/or the methods described below can be performed. As noted above, the vehicle 110 can alternatively be an automobile (e.g., a car, a truck, a bus, and/or a van), a railed vehicle (e.g., a train and/or a tram), a watercraft (e.g., a ship and/or a boat), and/or a spacecraft in other examples.

FIG. 2A depicts a perspective view of the aircraft 210 in accordance with an example embodiment. As shown in FIG. 2A, the aircraft 210 includes a propulsion system 240 having two turbofan engines 242; however, the propulsion system 240 can include a different quantity and/or type of engines 242 in alternative examples. The engines 242 are each coupled to a respective wing 244 of the aircraft 210. In an additional or alternative example, the engines 242 can be coupled to a fuselage 246 and/or an empennage 248 of the aircraft 210. The empennage 248 can support, for example, a pair of horizontal stabilizers 250 and a vertical stabilizer 252.

The fuselage 246 of the aircraft 210 defines an internal cabin, which can include a cockpit, one or more work sections (e.g., one or more galleys, lavatories, and/or personnel carry-on baggage areas), and one or more passenger sections (e.g., first class, business class, and coach sections). FIG. 2B depicts a top plan view of an internal cabin 254 of the aircraft 210, according to an example embodiment. As shown in FIG. 2B, the internal cabin 254 can include a front galley system 256 and a rear galley system 258, which each include electrical devices for performing galley operations.

Also, as shown in FIG. 2B, the aircraft 210 can include an electrical equipment bay 260 at a fore position of the aircraft 210 (e.g., in the fuselage 246 below the internal cabin 254). The electrical equipment bay 260 can receive power generated by the engines 242 and facilitate distributing the power to various commodity systems of the aircraft 210 (e.g., to the front galley system 256 and the rear galley system 258). For example, in FIG. 2B, the aircraft 210 includes a first commodity power feeder 216A that provides power from the electrical equipment bay 260 to the front galley system 256 and a second commodity power feeder 216B that provides power from the electrical equipment bay 260 to the rear galley system 258. As such, the first commodity power feeder 216A and the second commodity power feeder 216B extend from the electrical equipment bay 260 at a fore position of the aircraft 210 to the front galley system 256 and the rear galley system 258, respectively, at aft positions of the aircraft 210.

Additionally, the internal cabin 254 can include a first group of lavatories 262 adjacent to the front galley system 256, a second group of lavatories 264 between the front galley system 256 and the rear galley system 258, and a third lavatory 266 adjacent to the rear galley system 258. In this example, the first group of lavatories 262 can include a first disinfection system 200A, the second group of lavatories 264 can include a second disinfection system 200B, and the third lavatory 266 can include a third disinfection system 200C. Each disinfection system 200A, 200B, 200C can include one or more UV light sources 118, switches 126, power converters 128, control devices 130, power sensors 132, user input devices 136, and/or trigger sensors 138, as described above. In one implementation, for instance, each of the lavatories 262, 264, 266 can include a respective UV light source 118 that can emit the UV light 120 to disinfect the environment in the lavatory 262, 264, 266.

In this arrangement, the first disinfection system 200A can be selectively coupled to the first commodity power feeder 216A, whereas the second disinfection system 200B and the third disinfection system 200C can be selectively coupled to the second commodity power feeder 216B, as described above. As shown in FIG. 2B, the first disinfection system 200A is closer to the first commodity power feeder 216A than the electrical equipment bay 260, the second disinfection system 200B is closer to the second commodity power feeder 216B than the electrical equipment bay 260, and the third disinfection system 200C is closer to the second commodity power feeder 216B than the electrical equipment bay 260. Accordingly, because the disinfection systems 200A, 200B, 200C are coupled to the commodity power feeders 216A, 216B, the disinfection systems 200A, 200B, 200C can be provided in the aircraft 210 with reduced (or minimized) quantities and/or lengths of power feeders than would otherwise be required to directly couple the disinfection systems 200A, 200B, 200C to the electrical equipment bay 260. This can make installing and operating the disinfection systems 200A, 200B, 200C easier and more efficient.

In operation, the commodity power feeder 116, 216A, 216B can provide power from the power source 112 to the commodity system 114 (e.g., the front galley system 256 and/or the rear galley system 258 in FIG. 2B). The commodity system 114 can use the power received from the power source 112, via the commodity power feeder 116, 216A, 216B, to perform one or more operations of the commodity system 114 (e.g., storing, preparing, and/or cooking food and/or beverages).

While the commodity power feeder 116, 216A, 216B provides the power to the commodity system 114, the switch 126 can initially be in the first state such that the switch 126 decouples the UV light source 118 from the power on the commodity power feeder 116, 216A, 216B. The power sensor 132 can then measure the amount of power on the commodity power feeder 116, 216A, 216B and transmit a sensor signal to the control device 130 indicating the measured amount of power. The control device 130 can determine, based on the sensor signal, when the measured amount of power is less than the threshold amount of power. Responsive to the determination that the measured amount of power is less than the threshold amount of power, the control device 130 can actuate the switch 126 to the second state in which the switch 126 couples the UV light source 118 to the power on the commodity power feeder 116, 216A, 216B.

While the switch 126 couples the UV light source 118 to the power on the commodity power feeder 116, 216A, 216B, the control device 130 can activate the UV light source 118 using the power from the commodity power feeder 116, 216A, 216B. For instance, the control device 130 can activate the UV light source 118 responsive to one or more trigger signals received from the trigger sensors 138, as described above.

The power sensor 132 can continue to measure the power on the commodity power feeder 116, 216A, 216B and transmit sensor signals indicating the measured power to the control device 130. When the control device 130 determines that the measured power is greater than the threshold power, the control device 130 can actuate the switch 126 to the first state to decouple the UV light source 118 from the commodity power feeder 116, 216A, 216B. This process of measuring the amount of power on the commodity power feeder 116, 216A, 216B, actuating the switch 126 based on the measured amount of power, and activating the UV light source 118 can continue during operation of the vehicle 110.

Within examples, while coupling the UV light source 118 to the power on the commodity power feeder 116, 216A, 216B, the disinfection system 100, 200A, 200B, 200C can allow for using the power on the commodity power feeder 116, 216A, 216B to simultaneously (i) activate the UV light source 118 to emit the UV light 120 in the lavatory 122 of the vehicle 110 and (ii) operate an electrical device 115 in the commodity system 114. As described above, the threshold amount of power used by the control device 130 to control actuation of the switch 126 can be configured such that interrupting operation of the commodity system 114 is mitigated (or prevented). For instance, while activating the UV light source 118 and operating the electrical device 115 of the commodity system 114, the control device 130 can determine that the measured amount of power is greater than the threshold amount of power and responsively decouple the UV light source 118 from the power on the commodity power feeder 116, 216A, 216B to deactivate the UV light source 118 while continuing to operate the electrical device 115.

Figure 3:
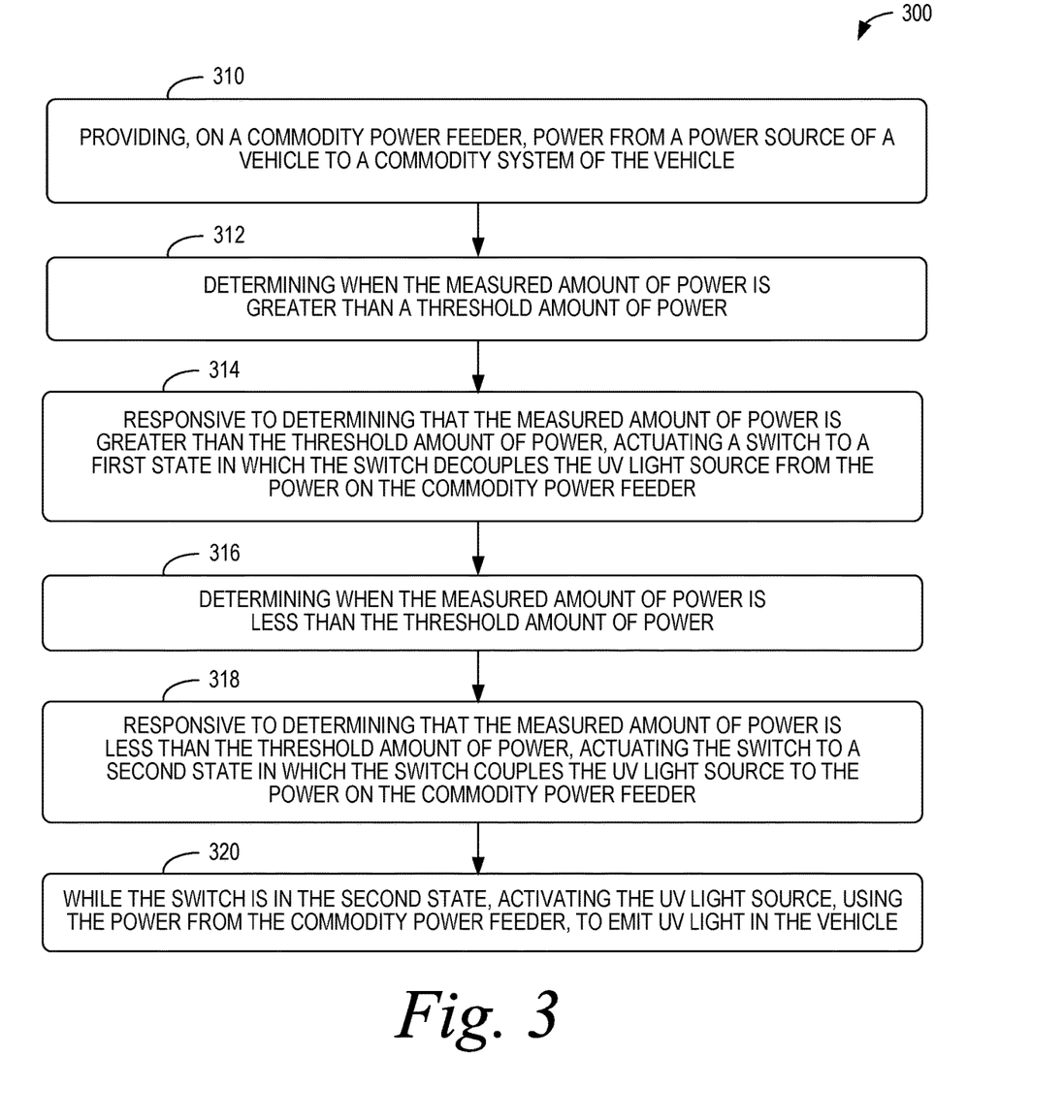
FIG. 3 illustrates a flow chart of an example process for operating a UV light source for a vehicle according to an example embodiment.

Referring now to FIG. 3, a flowchart for a process 300 of operating a UV light source for a vehicle is illustrated according to an example embodiment. As shown in FIG. 3, at block 310, the process 300 includes measuring an amount of power on a commodity power feeder, which provides the power from a power source of the vehicle to a commodity system of the vehicle. At block 312, the process 300 includes determining when the measured amount of power is greater than a threshold amount of power. At block 314, the process 300 further includes, responsive to determining that the measured amount of power is greater than the threshold amount of power, actuating a switch to a first state in which the switch decouples the UV light source from the power on the commodity power feeder.

At block 316, the process 300 includes determining when the measured amount of power is less than the threshold amount of power. At block 318, responsive to determining that the measured amount of power is less than the threshold amount of power, the process 300 includes actuating the switch to a second state in which the switch couples the UV light source to the power on the commodity power feeder. At block 320, the process 300 includes, while the switch is in the second state, activating the UV light source, using the power from the commodity power feeder, to emit UV light in the vehicle.

Figure 4:
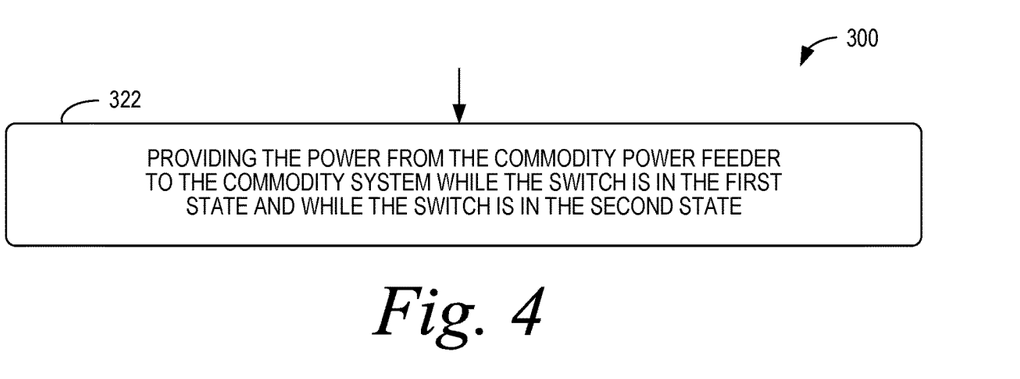
FIG. 4 illustrates a flow chart of an example process for operating a UV light source for a vehicle that can be used with the process shown in FIG. 3.
Figure 5:
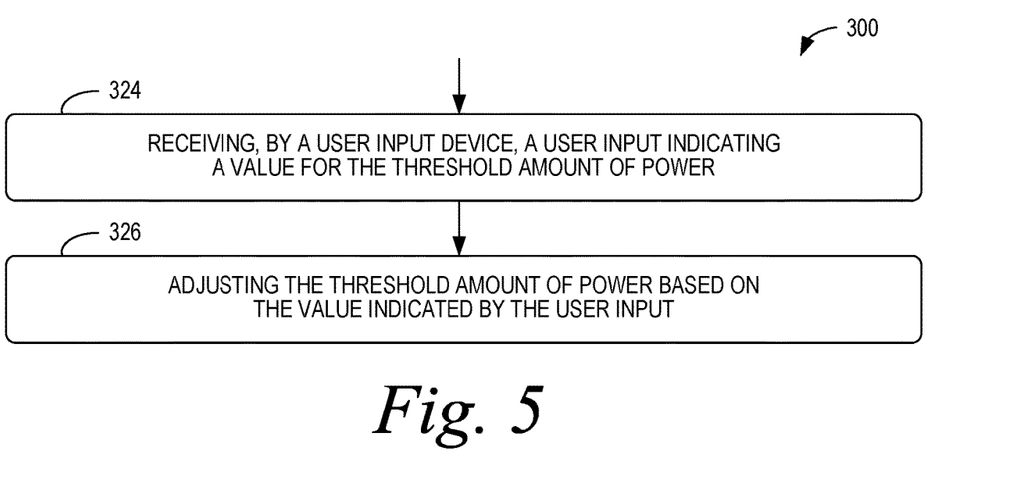
FIG. 5 illustrates a flow chart of an example process for operating a UV light source for a vehicle that can be used with the process shown in FIGS. 3-4.

FIGS. 4-7 depict additional aspects of the process 300 according to further examples. As shown in FIG. 4, the process 300 can include providing the power from the commodity power feeder to the commodity system while the switch is in the first state and while the switch is in the second state at block 322. As shown in FIG. 5, the process 300 can include receiving, by a user input device, a user input indicating a value for the threshold amount of power at block 324, and adjusting the threshold amount of power based on the value indicated by the user input at block 326.

Figure 6:
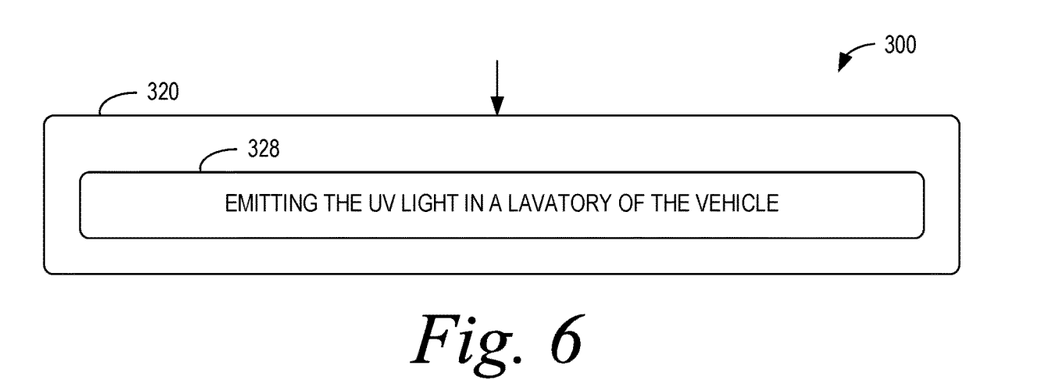
FIG. 6 illustrates a flow chart of an example process for operating a UV light source for a vehicle that can be used with the process shown in FIGS. 3-5.
Figure 7:
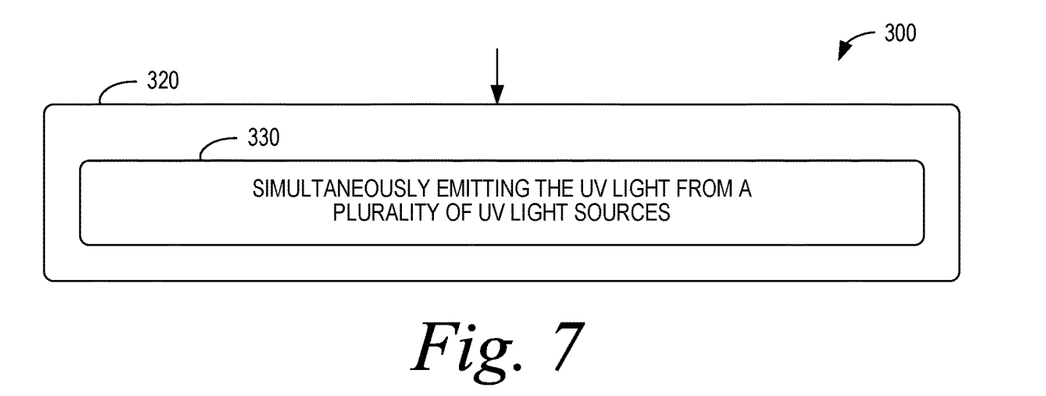
FIG. 7 illustrates a flow chart of an example process for operating a UV light source for a vehicle that can be used with the process shown in FIGS. 3-6.

As shown in FIG. 6, the commodity system can be a galley system of the vehicle and activating the UV light source at block 320 can include emitting the UV light in a lavatory of the vehicle at block 328. As shown in FIG. 7, activating the UV light source at block 320 can include simultaneously emitting the UV light from a plurality of UV light sources at block 330.

Figure 8:
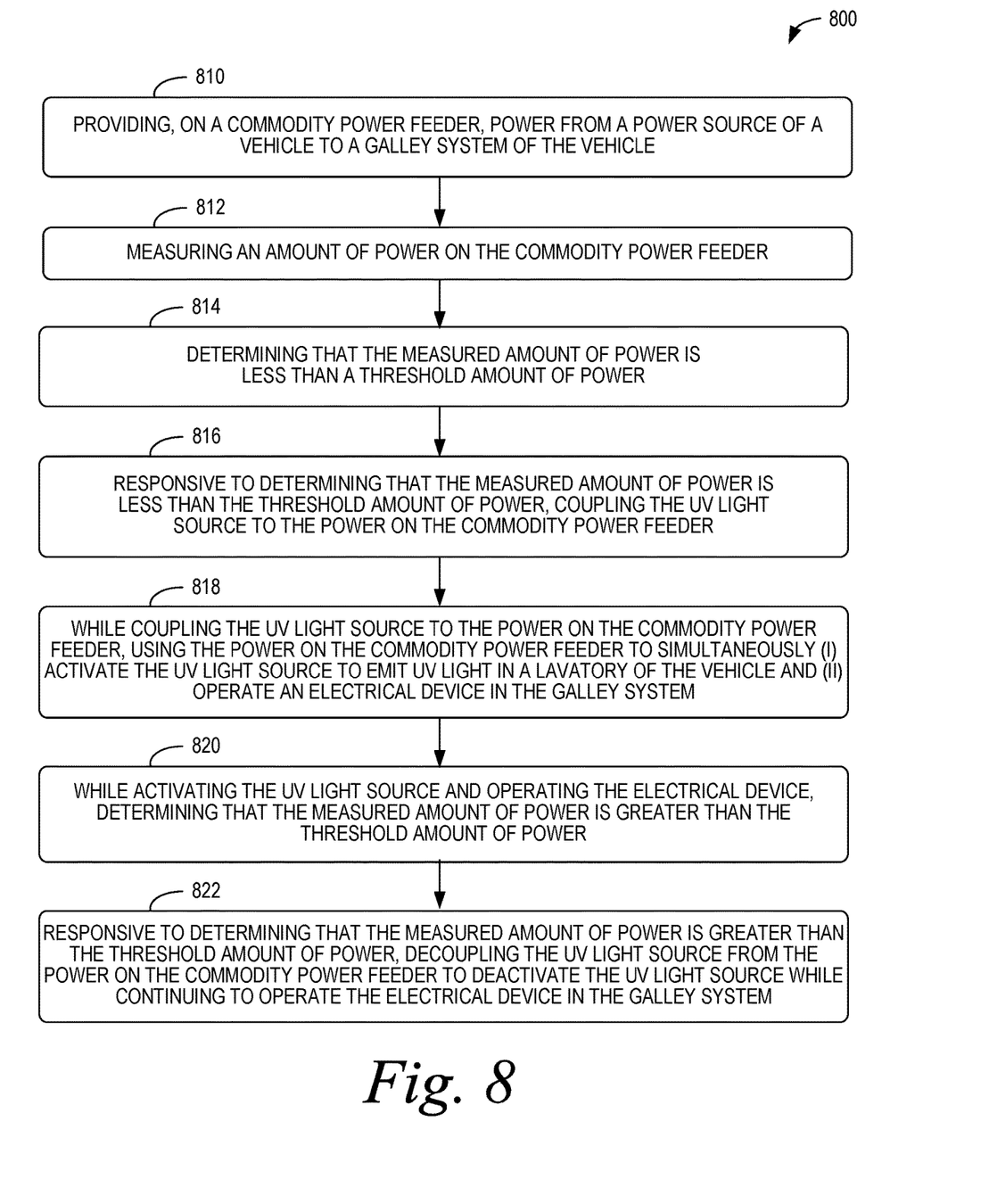
FIG. 8 illustrates a flow chart of an example process for operating a UV light source for a vehicle according to an example embodiment.

Referring now to FIG. 8, a flowchart for a process 800 of operating a UV light source is illustrated according to an example embodiment. As shown in FIG. 8, at block 810, the process 800 includes providing, on a commodity power feeder, power from a power source of a vehicle to a galley system of the vehicle. At block 812, the process 800 includes measuring an amount of power on the commodity power feeder. At block 814, the process 800 includes determining that the measured amount of power is less than a threshold amount of power. At block 816, the process 800 includes responsive to determining that the measured amount of power is less than the threshold amount of power at block 814, coupling the UV light source to the power on the commodity power feeder.

While coupling the UV light source to the power on the commodity power feeder at block 816, the process 800 includes using the power on the commodity power feeder to simultaneously (i) activate the UV light source to emit UV light in a lavatory of the vehicle and (ii) operate an electrical device in the galley system at block 818. While activating the UV light source and operating the electrical device at block 818, the process 800 includes determining that the measured amount of power is greater than the threshold amount of power at block 820. At block 822, the process 800 includes, responsive to determining that the measured amount of power is greater than the threshold amount of power at block 820, decoupling the UV light source from the power on the commodity power feeder to deactivate the UV light source while continuing to operate the electrical device in the galley system.

Figure 9:
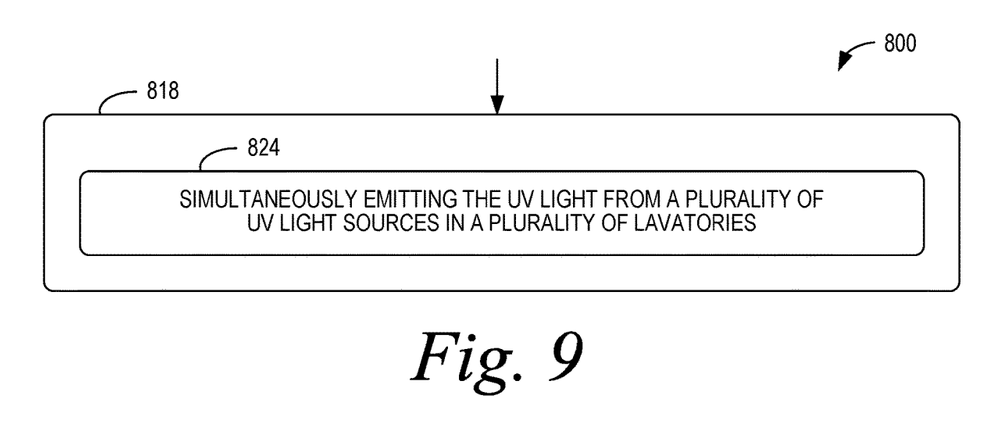
FIG. 9 illustrates a flow chart of an example process for operating a UV light source for a vehicle that can be used with the process shown in FIG. 8.

FIG. 9 depicts additional aspects of the process 800 according to further examples. As shown in FIG. 9, activating the UV light source at block 818 includes simultaneously emitting the UV light from a plurality of UV light sources in a plurality of lavatories at block 824.

Any of the blocks shown in FIGS. 3-9 may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In some instances, components of the devices and/or systems described herein may be configured to perform the functions such that the components are actually configured and structured (with hardware and/or software) to enable such performance. Example configurations then include one or more processors executing instructions to cause the system to perform the functions. Similarly, components of the devices and/or systems may be configured so as to be arranged or adapted to, capable of, or suited for performing the functions, such as when operated in a specific manner.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to explain the principles of the embodiments, the practical application, and to enable others of ordinary skill in the art to understand the disclosure for various embodiments with various modifications as are suited to the particular use contemplated.

What is claimed is:

1. A disinfection system for a vehicle, comprising:
    an ultraviolet (UV) light source configured to emit UV light in the vehicle;
    a switch configured to selectively couple the UV light source to a commodity power feeder, wherein the commodity power feeder provides power from a power source of the vehicle to a commodity system of the vehicle, wherein the switch is actuatable between:
        a first state in which the switch decouples the UV light source from the power on the commodity power feeder, and
        a second state in which the switch couples the UV light source to the power on the commodity power feeder;
    a power sensor configured to measure an amount of power on the commodity power feeder; and
    a control device in communication with the power sensor and the switch, wherein the control device is configured to:
        determine when the measured amount of power is greater than a threshold amount of power,
        responsive to a determination that the measured amount of power is greater than the threshold amount of power, actuate the switch to the first state,
        determine when the measured amount of power is less than the threshold amount of power, and
        responsive to a determination that the measured amount of power is less than the threshold amount of power, actuate the switch to the second state.

2. The disinfection system of claim 1, wherein the switch is coupled to the commodity power feeder such that the commodity power feeder provides the power from the power source to the commodity system when the switch is in the first state and when the switch is in the second state.

3. The disinfection system of claim 1, wherein the threshold amount of power is less than a peak amount of power, which is related to a predetermined peak loading of the commodity system.

4. The disinfection system of claim 1, further comprising a user input device, wherein the user input device is in the vehicle, wherein the user input device is in communication with the control device, and wherein the user input device is configured to:
    receive a user input indicating a value for the threshold amount of power; and
    transmit an input signal to the control device to cause the control device to adjust the threshold amount of power based on the value indicated by the user input.

5. The disinfection system of claim 1, wherein the UV light source is configured to emit the UV light at a wavelength in a range of approximately 190 nm to approximately 240 nm.

6. The disinfection system of claim 1, wherein the UV light source comprises a plurality of UV light sources,
    wherein the plurality of UV light sources are configured to simultaneously emit the UV light using power received from the commodity power feeder while the switch is in the second state.

7. A vehicle comprising:
    a commodity power feeder;
    a commodity system, wherein the commodity system is a galley system of the vehicle; and
    a disinfection system comprising:
        an ultraviolet (UV) light source configured to emit UV light in the vehicle;
        a switch configured to selectively couple the UV light source to the commodity power feeder, wherein the commodity power feeder provides power from a power source of the vehicle to the commodity system of the vehicle, wherein the switch is actuatable between:
            a first state in which the switch decouples the UV light source from the power on the commodity power feeder, and
            a second state in which the switch couples the UV light source to the power on the commodity power feeder;
        a power sensor configured to measure an amount of power on the commodity power feeder; and
        a control device in communication with the power sensor and the switch, wherein the control device is configured to:
            determine when the measured amount of power is greater than a threshold amount of power,
            responsive to a determination that the measured amount of power is greater than the threshold amount of power, actuate the switch to the first state, determine when the measured amount of power is less than the threshold amount of power, and responsive to a determination that the measured amount of power is less than the threshold amount of power, actuate the switch to the second state, wherein the threshold amount of power is less than a peak amount of power, which is related to a predetermined peak loading of the commodity system.

8. The vehicle of claim 7, wherein the commodity power feeder extends from a forward electrical equipment bay at a fore position of the vehicle to the galley system at an aft position of the vehicle.

9. The vehicle of claim 8, wherein the power sensor is at a position along the commodity power feeder between the forward electrical equipment bay and the galley system.

10. The vehicle of claim 7, wherein the UV light source is in a lavatory of the vehicle.

11. The vehicle of claim 7, wherein the switch is coupled to the commodity power feeder such that the commodity power feeder provides the power from the power source to the commodity system when the switch is in the first state and when the switch is in the second state.

12. The vehicle of claim 7, further comprising a user input device, wherein the user input device is in the vehicle, wherein the user input device is in communication with the control device, and wherein the user input device is configured to:

receive a user input indicating a value for the threshold amount of power; and transmit an input signal to the control device to cause the control device to adjust the threshold amount of power based on the value indicated by the user input.

13. The vehicle of claim 7, wherein the UV light source is configured to emit the UV light at a wavelength in a range of approximately 190 nm to approximately 240 nm.

14. A method of operating a ultraviolet (UV) light source for a vehicle, comprising:

providing a disinfection system comprising:

the UV light source configured to emit UV light in the vehicle, a switch configured to selectively couple the UV light source to a commodity power feeder, wherein the commodity power feeder provides power from a power source of the vehicle to a commodity system of the vehicle, wherein the switch is actuatable between, a first state in which the switch decouples the UV light source from the power on the commodity power feeder, a second state in which the switch couples the UV light source to the power on the commodity power feeder, a power sensor configured to measure an amount of power on the commodity power feeder; and a control device in communication with the power sensor and the switch;

measuring an amount of power on the commodity power feeder, which provides the power from the power source of the vehicle to the commodity system of the vehicle;

determining, using the control device, when the measured amount of power is greater than a threshold amount of power;

responsive to determining that the measured amount of power is greater than the threshold amount of power, actuating the switch to the first state in which the switch decouples the UV light source from the power on the commodity power feeder;

determining, using the control device, when the measured amount of power is less than the threshold amount of power;

responsive to determining that the measured amount of power is less than the threshold amount of power, actuating the switch to the second state in which the switch couples the UV light source to the power on the commodity power feeder; and while the switch is in the second state, activating the UV light source, using the power from the commodity power feeder, to emit UV light in the vehicle.

15. The method of claim 14, further comprising providing the power from the commodity power feeder to the commodity system while the switch is in the first state and while the switch is in the second state.

16. The method of claim 14, wherein the threshold amount of power is less than a peak amount of power, which is related to a predetermined peak loading of the commodity system.

17. The method of claim 14, further comprising:

receiving, by a user input device, a user input indicating a value for the threshold amount of power; and adjusting the threshold amount of power based on the value indicated by the user input.

18. The method of claim 14, wherein the step of activating the UV light source comprises emitting the UV light at a wavelength of approximately 190 nm to approximately 240 nm.

19. The method of claim 14, wherein the commodity system is a galley system of the vehicle, and wherein the step of activating the UV light source comprises emitting the UV light in a lavatory of the vehicle.

20. The method of claim 14, wherein the step of activating the UV light source comprises simultaneously emitting the UV light from a plurality of UV light sources.

* * * * *